United States Patent
Jackman (10) Patent No.: US 7,067,801 B2
(45) Date of Patent: Jun. 27, 2006

(54) MASS SPECTROMETRIC ANALYSIS OF COMPLEX MIXTURES OF IMMUNE SYSTEM MODULATORS

(75) Inventor: Joany Jackman, Walkersville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/470,877

(22) PCT Filed: Feb. 1, 2002

(86) PCT No.: PCT/US02/03180

§ 371 (c)(1),
(2), (4) Date: Jul. 31, 2003

(87) PCT Pub. No.: WO02/061409

PCT Pub. Date: Aug. 8, 2002

(65) Prior Publication Data

US 2004/0089800 A1    May 13, 2004

Related U.S. Application Data

(60) Provisional application No. 60/265,797, filed on Feb. 1, 2001.

(51) Int. Cl.
*H01J 49/04* (2006.01)
(52) U.S. Cl. .................................. 250/282; 250/288
(58) Field of Classification Search ............... 250/281, 250/289, 287, 288, 282; 536/23.5; 600/532; 436/173; 435/6

See application file for complete search history.

(56) References Cited

U.S. PATENT DOCUMENTS

| 3,842,266 A | * | 10/1974 | Thomas ...................... 250/288 |
| 5,081,871 A | * | 1/1992 | Glaser ...................... 73/863.23 |
| 5,202,563 A | * | 4/1993 | Cotter et al. ................ 250/287 |
| 5,572,025 A | * | 11/1996 | Cotter et al. ................ 250/292 |
| 5,627,369 A | | 5/1997 | Vestal et al. |
| 5,645,072 A | * | 7/1997 | Thrall et al. ................. 600/532 |
| 5,668,373 A | * | 9/1997 | Robbat et al. ......... 250/339.12 |

(Continued)

FOREIGN PATENT DOCUMENTS

DE    195 22 774 A1    1/1997

OTHER PUBLICATIONS

Mutlu, G. M., K. W. Garey, et al. (2001). "Collection and analysis of Exhaled Breath Condensate in humans." Am J Respir Crit Care Med 164(5): 731-737.*

(Continued)

*Primary Examiner*—Kiet T. Nguyen
(74) *Attorney, Agent, or Firm*—Albert J. Fasulo, II (57) ABSTRACT

The invention is directed to methods suitable for detecting the presence of a plurality of immune system modulators in a complex solution by running a single sample through a mass spectrometer without any surface preparation or preliminary purification step. Immune system modulators that can be analyzed with the methods of the present invention include cytokines (interferons and interleukins), chemokines, host cell response molecules, and peptide fragments. The method also allows the identification of truncated receptors for immune modulators secreted by infected cells or pathogens, such as virokines, and other pathogen-encoded proteins that affect the host immune system.

24 Claims, 5 Drawing Sheets

U.S. PATENT DOCUMENTS

| | | | |
|---|---|---|---|
| 5,742,049 A * | 4/1998 | Holle et al. | 250/282 |
| 5,935,803 A | 8/1999 | Vasquez et al. | |
| 5,955,731 A * | 9/1999 | Bergmann et al. | 250/288 |
| 5,962,244 A | 10/1999 | Lynch et al. | |
| 6,160,255 A * | 12/2000 | Sausa | 250/227.24 |
| 6,363,772 B1 * | 4/2002 | Berry | 73/24.02 |
| 6,414,306 B1 * | 7/2002 | Mayer-Posner et al. | 250/288 |
| 6,508,986 B1 * | 1/2003 | Anderson et al. | 422/100 |
| 6,585,661 B1 * | 7/2003 | Hunt et al. | 600/532 |
| 6,599,253 B1 * | 7/2003 | Baum et al. | 600/532 |
| 2002/0055186 A1 * | 5/2002 | Barry et al. | 436/518 |
| 2002/0151707 A1 * | 10/2002 | Kindsvogel et al. | 536/23.5 |

OTHER PUBLICATIONS

"Exhaled breath condensate isoprostanes are elevated in patients with acute lung injury or ARDS", Carpenter et al, American College of Chest Physicians, Dec. 1988, vol. 114, iss.6, pp. 1653-1660.*

"Detection of nonvolatile macromolecules in breath. A possible diagnostic tool?" authored by Scheideler et al, Am. Rev. Respir Dis. vol. 148 (3), 1993, p. 778-84 (see abstract).*

PCT International Search Report-PCT/US02/03180.

* cited by examiner

FIG. 1

FIG 2
Detection of Cytokines by Gridless MALDI-TOF Mass Spectrometer

FIG. 3

Comparison of Cytokine Spectral Profile

Individual Cytokine Spectra Overlaid and Calibrated to Same Intensity Scale

FIG. 4 Cytokine Detection in Complex Backgrounds

FIG. 5 Detection of Cytokines by MALDI-TOF Mass Spectrometer with Acceleration Grid Under conditions where IL-6 is visible, we can not detect other cytokines.

MASS SPECTROMETRIC ANALYSIS OF COMPLEX MIXTURES OF IMMUNE SYSTEM MODULATORS

CROSS-REFERENCE TO RELATED APPLICATIONS

This application claims the benefit of prior now abandoned U.S. Provisional Application No. 60/265,797, filed on Feb. 1, 2001, the contents of which are hereby incorporated by reference. This application also hereby incorporates by reference the contents of a related U.S. application, filed on Feb. 1, 2002, entitled Diagnosis of Pathogen Infections using Mass Spectral Analysis of Immune Modulators in Post-exposure Biological Samples, Jackman.

STATEMENT OF GOVERNMENTAL INTEREST

This invention was made with U.S. Government Support under the Defense Advanced Research Projects Agency (DARPA) Contract No. DABT-63-99-0021. The U.S. Government has certain rights in the invention.

BACKGROUND OF THE INVENTION

1. Field of the Invention

This invention is in the field of mass spectrometric analysis of multiple immune system modulators in a complex mixture. Immune system modulators typically have molecular masses of less than about 30 kilo Daltons, and include chemokines and cytokines (which encompass interferons and interleukins) and arachidonic acid metabolites.

2. Description of the Related Art

There is a great need in the biotechnology industry for a method that would permit the rapid and accurate identification of immune system modulators in a complex mixture, for example, a biological sample. Such immune system modulators include chemokines and cytokines (which encompass using interferons and interleukins). Immune modulators also include arachidonic acid metabolites and truncated receptors for immune modulators secreted by infected cells or pathogens to manipulate the host immune system, such as virokines, and other pathogen-encoded proteins that affect the host immune system, host cell response molecules, and peptide fragments.

Cytokines are a varied group of proteins that are released by mammalian cells and act on other cells through specific receptors through which they elicit a wide variety of responses affecting the immune system. Cytokine actions include control of cell proliferation and differentiation, regulation of immune responses, hemopoiesis and inflammatory responses. Included among the cytokines are growth factors, interferons, interleukins and tumor necrosis factors. The majority of cytokines has molecular masses below 30 kilo Daltons in their monomeric form, and most have molecular masses in the ranges of 8,000–10,000 Daltons or 15,000–20,000 Daltons. A Dalton is a unit of atomic and molecular mass, equal to one-twelfth of the mass of the nuclide carbon-12. It is identical with the unified atomic mass unit.

Chemokines are other immune system modulators that constitute a super family of soluble proteins implicated in a wide range of acute and inflammatory processes and other immunoregulatory functions.

Chemokines and cytokines are nearly indistinguishable on SDS PAGE (sodium dodecyl sulfate polyacrylamide gel electrophoresis) gels based on the relative molecular mobility at this level of resolution. The most widely used method for identifying cytokines in a complex mixture is the Enzyme Linked Immunosorbent Assay (ELISA), which antigenically distinguishes cytokines (Balkwill, Cytokines—a practical approach. Oxford University Press, New York. 1991). ELISAs are expensive and time consuming, taking more than 90 minutes to complete. Moreover, there is significant cross-sensitivity between a given antibody to a cytokine and other closely related cytokines in the same class which causes inaccuracies, for example among the interferons and interleukins. Further, ELISAs only permit analysis of one cytokine at a time, therefore a separate ELISA has to be run to detect each unique cytokine in a complex mixture.

Even mass spectrometry with its high resolving power for low molecular mass species, cannot identify cytokines and other immune system modulators in a complex mixture.

Many studies have been reported showing that infection of an animal by a pathogen causes dramatic changes in the expression of one or more immune modulators in the animal at the site of infection. However, the techniques available for detecting the presence of immune system modulators in a complex mixture are slow, expensive, sometimes unreliable, and technically difficult to perform, thus making it impractical to monitor changes in immune modulators in biological samples in real time as a diagnostic tool for diagnosing infectious diseases in large numbers of people such as might be infected in a terrorist attack using biological weapons. A rapid and accurate method for detecting the presence or absence of immune modulators in biological samples in real time or near real time would open the door for developing new tools to diagnose infections, and for monitoring disease progression.

Based on the foregoing, there is a clear need for a rapid, sensitive and affordable method for detecting multiple immune system modulators in a complex mixture.

SUMMARY OF THE INVENTION

In one aspect of the invention, techniques are provided for analyzing the presence of one or more immune system modulators in a complex mixture using mass spectrometry, including obtaining a complex mixture for mass spectral analysis, putting a sample of the complex mixture on a substratum suitable for use in a mass spectrometer, saturating the sample with matrix material, allowing the matrix-saturated sample to dry, inserting the sample into a gridless mass spectrometer, processing the sample in the gridless mass spectrometer to obtain a mass spectrograph of the complex mixture. Immune system modulators that can be analyzed with the methods of the present invention include cytokines (interferons and interleukins), chemokines, truncated receptors for immune modulators secreted by infected cells or pathogens, host cell response molecules, and peptide fragments. The present method can also be used to identify other molecular infection markers in a complex mixture such as pathogen-encoded proteins or peptides, prions, and pathogen-encoded DNA. The method can also further include obtaining a known sample of pure immune system modulator standard for a particular immune system modulator, putting the known sample on a substratum suitable for use in a mass spectrometer, repeating the saturating, drying and processing steps for the known sample to obtain a mass spectrograph of the pure immune system modulator standard, comparing the mass spectrograph of the complex mixture to the mass spectrograph of the pure immune system modulator standard, and determining whether the complex mixture includes the particular immune system modulator based on whether one or more peaks of the mass spectrograph of the pure immune system modulator standard are identified in the mass spectrograph of the complex mixture.

In embodiments of this aspect, the complex mixture is a biological sample that may be bronchial lavage, sputum, saliva or exhaled breath condensate, in which case there is no requirement for a pre-purification of the biological sample. If the biological sample is urine, it may require a wash to remove unwanted ions before mass spectral analysis. In some embodiments the mass spectrometer is a matrix assisted laser desorption/ionization (MALDI) mass spectrometer. In some embodiments the mass spectrometer is operated in a linear mode. In some embodiments it is operated in a reflectron mode. The mass spectrograph is obtained with pulsed extraction in some embodiments and without pulsed extraction in some embodiments. In some embodiments, the matrix for detecting immune system modulators is a sinapinic acid matrix. Post-source decay (PSD) analysis is used in some embodiments to resolve immune modulators that have the same or close molecular mass. In various embodiments ultraviolet lasers or infrared lasers are used.

BRIEF DESCRIPTION OF THE DRAWINGS

The present invention is illustrated by way of example, and not by way of limitation, in the figures of the accompanying drawings.

FIG. 2 is a graph illustrating Detection of Cytokines by Gridless MALDI-TOF (matrix-assisted laser desorption/ionization, time of flight) Mass Spectrometer, that shows four mass spectrographs run on a Kratos MALDI-TOF gridless mass spectrometer in the linear mode. The spectrographs show femtomolar amounts of pure bovine serum albumin (BSA) run alone (FIG. 2A); TNF-alpha (rh) with a large molar excess of BSA (FIG. 2B); IL1-alpha (rh) mixed with a large molar excess of BSA (FIG. 2C); and IL-6 (rh) with a large molar excess of BSA (FIG. 2D).

FIG. 4 is a graph illustrating Cytokine Detection in complex Backgrounds, that shows the mass spectrographs of sputum (4A); sputum plus BSA (4B); equal amounts of three cytokines IL-6, TNF alpha and IL-1 alpha in a 1:1:1 ratio with a large excess of BSA in complex mixture of 1:1 sputum to cytokines (4C); and of the three cytokines IL-6, TNF alpha and IL-1 alpha in a 1:1:10 ratio with a large excess of BSA in a complex mixture of 1:1 sputum to cytokines (4D).

DETAILED DESCRIPTION

The invention is directed to a method for detecting the presence of multiple immune system modulators in a complex solution by running a single sample through a gridless mass spectrometer without any surface preparation or preliminary purification step. A sample that can be mixed directly with a matrix for mass spectral analysis without any pre-purification step is hereinafter called a "neat" sample. Immune system modulators cannot be reliably detected in a complex mixture, or even in a simple mixture, operating a mass spectrometer with an acceleration grid. Immune system modulators that can be analyzed with the methods of the present invention include cytokines (interferons and interleukins), chemokines, truncated receptors for immune modulators secreted by infected cells or pathogens, host cell response molecules, and peptide fragments. The present method can also be used to identify other molecular markers of infection in a complex mixture such as pathogen-encoded proteins or peptides, prions, and pathogen-encoded DNA including fragments.

The introduction of the commercial matrix assisted laser desorption/ionization (MALDI) mass spectrometer instrument in 1988 provided a new and powerful technique for the analysis of large biological molecules, resulting in the commercialization of TOF (time of flight) mass spectrometers by a number of manufacturers (Noble, Anal. Chem. 67 497A–507A, 1995) (Karas, Anal. Chem. 60: 2299, 1988; Tanaka, Rapid Commun. Mass Spectrom. 2 151, 1988). In the simple (linear) TOF mass spectrometer, ions are formed and accelerated in a short source region. The ions' flight times (t) through a longer drift region (D) are measured to determine their mass (m) according to the equation:

$$t = \left(\frac{m}{2\,\text{eV}}\right)^{1/2} D$$

where eV=kinetic energy. The laser driven ionization of the source material is improved by mixing the material with an energy-absorbing matrix. The matrix assists ionization of the source material by transferring energy, hence the name MALDI-TOF mass spectrometry.

Some mass spectrometers have a "reflectron" to reflect ions back towards a rear-mounted detector, which effectively increases the flight tube length and thus improves resolution of the mass spectrographs. Focusing occurs as ions with higher kinetic energy are subjected to a greater reflecting voltage by passing deeper into the reflectron than those ions of the same molecular mass but lower kinetic energy. The reflectron helps to reduce the intrinsic heterogeneity of ion movement to the detector based on variations in initial kinetic energy. This phenomena is depicted below in a single-stage reflectron instrument (FIG. 1—Single-stage Reflectron TOF Mass Spectrometer) where s is the short source region 100, 2s defines the focusing region 102, L1 is the forward ion drift region 103, and L2 is the reverse ion drift region 104 and d represents the penetrance distance 105 into the reflectron voltage field 106. The heterogeneity of the ions' kinetic energy (eV) is represented by the band depicted as eV-Uo and eV+Uo. The focusing action of a reflectron results from the fact that equal mass ions with higher kinetic energies (eV+Uo) penetrate the reflectron more deeply, so that these faster ions spend more time in the reflectron and arrive at the detector at the same time as the slower ions (eV-Uo). As ions re-emerge from the reflectron, the grouped ion packets, though separated, are compressed in time and space, producing higher mass resolution.

Figure 1:
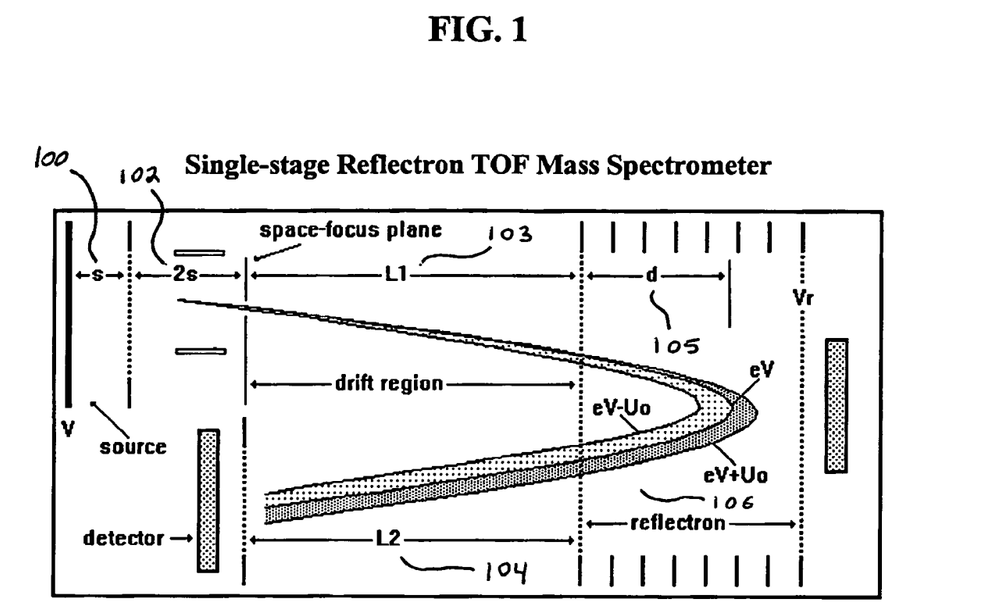
FIG. 1 is a block diagram of a Single-stage Reflectron TOF (time of flight) Mass Spectrometer.

Single-stage reflectrons are generally constructed as a series of resistively coupled lens elements whose voltages increase linearly to produce a constant retarding field. In commercial instruments designed for biological research, V is typically 10–20 kV for proteins and the drift region for the mass analyzer ranges from 0.5 to 3 meters. Dual-stage reflectrons that use two energy levels within region d are configured to further improve focusing while reducing the required length of the drift regions. This permits the construction of more compact reflectrons. Reflectron spectrometry may be used to detect cytokines if the reflectron is capable of reflecting the mass range that includes the mass of the cytokines in the sample. Reflectron spectrometry was not used to obtain any of the spectrographs in the figures.

In the MALDI-TOF mass spectrometer, low molecular mass compounds (less than about 30 kilo Daltons) generally may be fragmented inside the ion source providing significant structural information in the mass spectra. Such information can be obtained using either the linear or reflectron modes of the spectrometer. Because the excess energy from the ionization process is absorbed by a larger number of covalent bonds, higher molecular mass compounds will fragment over a longer time frame, with much of the fragmentation occurring in the drift region. The fragmentation pattern of a molecular ion is believed to be an intrinsic property of the molecule, therefore it is a unique "signature" for the respective molecule. Known as Post Source Decay (PSD) in the art, the product ions resulting from fragmentation of a molecular ion in the drift region will have a range of flight times permitting PSD analysis to be used to distinguish molecules of similar or the same molecular mass that cannot be distinguished by simple linear ionization techniques. PSD analysis is generally best suited to molecules in the 6–10 kDa range such as the immune system modulators listed in Table 1 (Cotter, Time-of-Flight Mass Spectrometry: Instrumentation and Applications in Biological Research, American Chemical Society, Washington, D.C. 1997).

TABLE 1

Characteristics of Known Inflammatory Cytokines*

| Cytokine | Predicted MW in kDa | Observed MW in kDA | Glycosylation (N, O—) | Immune Cell Source |
|---|---|---|---|---|
| TNFα | 26 | 17 | | T/M |
| IFNα | | 16–27 | N | T/M |
| IFNβ | | 20 | N | — |
| IFNK | 17.1 | 20, 25 | N | T |
| IL11,9 | 17.5, 17.3 | 17–20 | N | M |
| IL2 | 15.4 | 15–20 | O | T |
| IL4 | 15 | 15–19 | N | T |
| IL6 | 20.8 | 26 | N | T/M |
| IL8 | 11.1 | 6–8 | — | M |
| MIP1I,9 | 8.6, 8.6 | 8–200, 7.8 | O | M/T |
| MIP2 (GRO9) (GROK) | 11.4 | 7.9 | — | M |
| MCP1,2,3 | 8.7 | 8–18 | O | M |
| RANTES | 8 | 8 | O | T |
| GMCSF | 11.6 | 22 | N | T/M | as compiled from Callard 1994 and Vaddi 1997.
*MIP = Macrophage inflammatory protein; MCP = Monocyte chemoattractant protein; GMCSF = Granulocyte/Macrophage Colony Stimulating Factor; IL = Interleukin; IFN = Interferon; TNF = Tumor Necrosis Factor
**N = N linked; O = linked
***M = Macrophage/Monocyte Derived; T = T-cell Derived In order to use PSD analysis, the operator must know the pattern of cytokines or other immune system modulator that will be detected in the sample (or that the operator wishes to look for) before running the samples, because the operator must set a cut-off molecular mass to use this feature. Use of PSD analysis therefore optimizes the mass range for the fragments to be analyzed. PSD analysis is most advantageous for identifying and distinguishing among unique molecules that have the same molecular mass but different amino acid sequences, and that differ from one another by less than about 500 Daltons. PSD optimization was not used to generate any of the spectrographs in the figures herein because it was not needed to identify the cytokines even in neat samples.

Figure 2A:
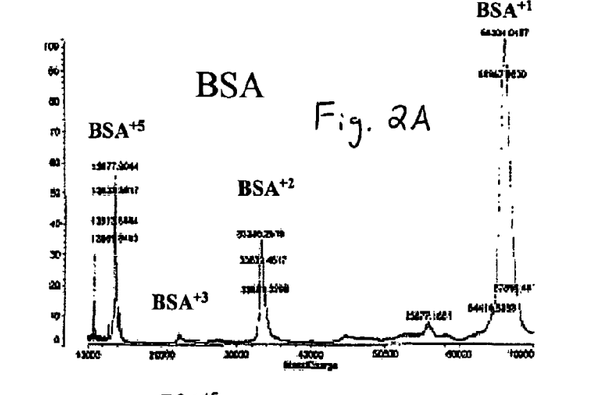
Figure 2B:
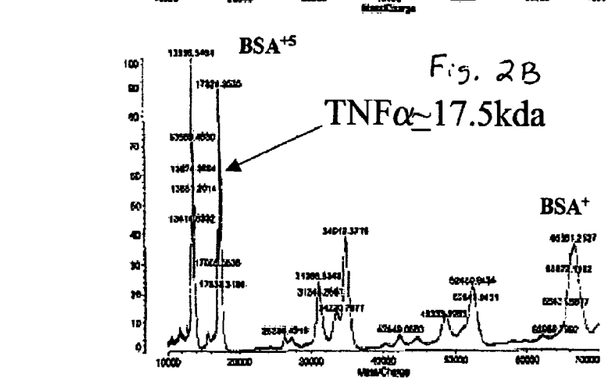
Figure 2C:
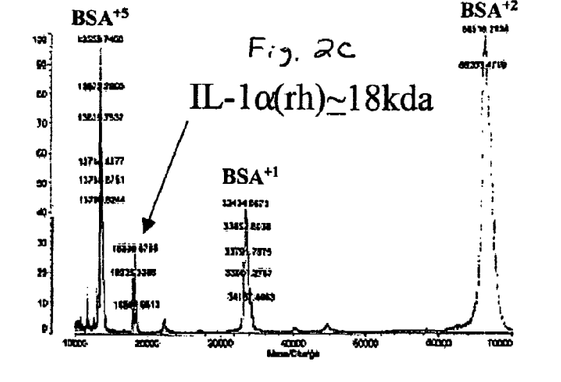
Figure 2D:
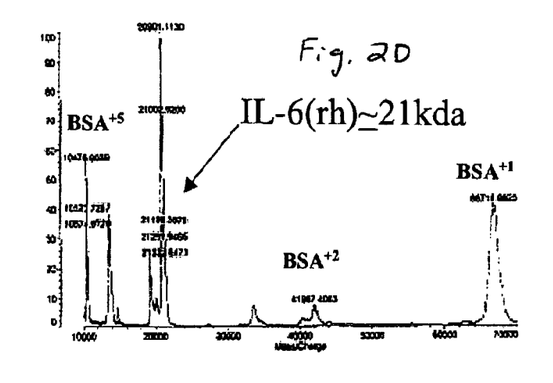

In a first experiment, mass spectrographs run were obtained on a gridless Kratos MALDI-TOF mass spectrometer operating in the linear mode using an ultraviolet laser for ionizing femtomole samples of bovine serum albumin (BSA) run alone and suspended in water (FIG. 2A); TNF-alpha(rh) with a large molar excess of BSA in water (FIG. 2B); IL1-alpha(rh) mixed with a large molar excess of BSA in water (FIG. 2C); and IL-6(rh) with a large molar excess of BSA in water (FIG. 2D). On the mass spectrograph of FIG. 2 and following figures, the scale of the signal intensity on the y-axis was maximized to the signal intensity for the peak at about 17,000, which corresponds to the peak of TNF-alpha (rh). As is shown in FIG. 2, one can readily detect femtomolar amounts of bovine serum albumin (BSA) run alone, and individual cytokines TNF-alpha(rh), IL-6(rh) and IL1-alpha(rh) mixed with a large molar excess of BSA. Infrared lasers also come within the scope of the present invention for using mass spectrometry to identify immune modulators in a complex-sample. All of the cytokines in the samples tested in the examples below are recombinant human proteins (rh). It should be noted that in freezing and thawing IL-6, the protein was truncated from its usual size of about 25 kilo Daltons, to 20 kilo Daltons. All of the cytokine samples were run in a matrix of sinapinic acid prepared in 70% acetonitrile (HPLC grade) and 30% acidified water (HPLC Grade).

Figure 3:
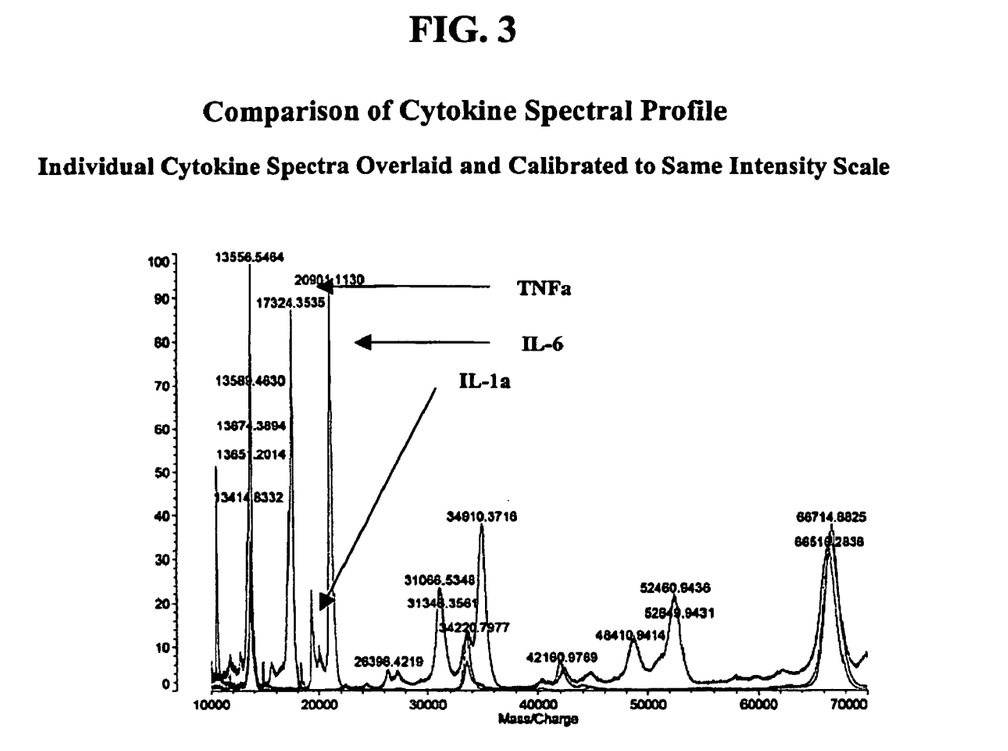
FIG. 3 is a graph illustrating Comparison of Cytokine Spectral Profile that shows the individual cytokine spectrographs from FIG. 2 overlaid and calibrated to the same intensity scale.

Looking at the individual mass spectrographs of the three cytokines in FIG. 2B, C and D, it appears that all three unique cytokines "fly equally" through the mass spectrometer which was operated in the linear mode without an acceleration grid, i.e., the ionized molecular ion of each of the different cytokines appear to go through the system the same way thereby giving a single peak in the same mass/charge range. Such a single peak in the same mass/charge range would seem to prevent the resolution of the individual cytokines if they were run together in a mixture; however, it was discovered that this is actually wrong. The mistaken impression that mass spectrometry can only detect a single cytokine in a mixture of cytokines results because each of the different cytokines run individually had been autoscaled by the mass spectrometer. In order to obtain a full-scale histogram, the three individual cytokine spectrographs were normalized to the same ionization signal, that being the highest ionization signal (i.e., the highest peak measured as mass/charge) of the three different cytokines being analyzed. For the three cytokines studied, it was the ionization signal for TNF alpha(rh). When each of the three spectrographs of the three respective cytokines run individually was normalized, overlaid and aligned, three distinct peaks at the respective masses for each cytokine could be identified. FIG. 3 shows that IL-1-alpha is very small peak resting to the right of large TNF alpha peak, and IL-6 is a separate peak to the right of IL-1 alpha. This discovery was quite impressive and unexpected since the molecular mass of TNF alpha and IL-1 alpha are only 500 Daltons apart, and since mass spectrometry was presumed to be unable to identify more than one cytokine in a complex mixture at a time.

Figure 4A:
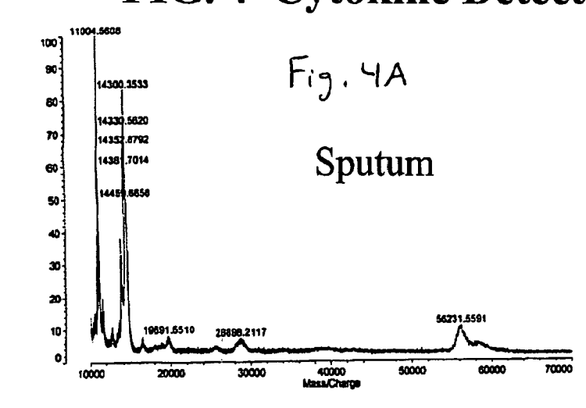
Figure 4B:
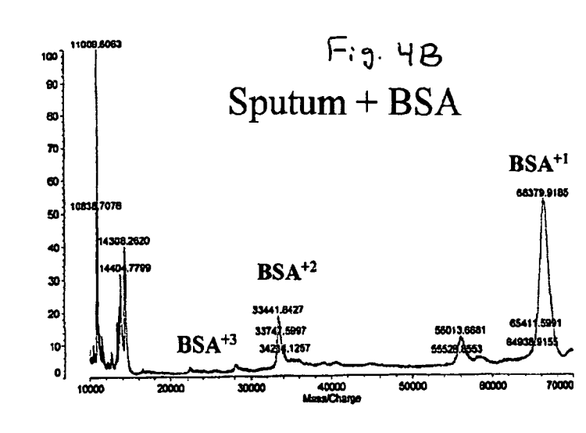
Figure 4C:
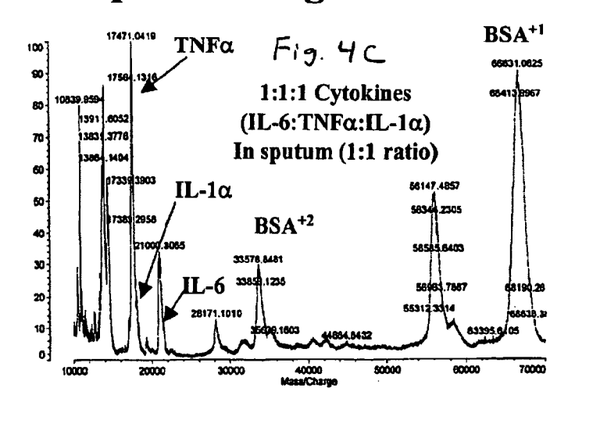
Figure 4D:
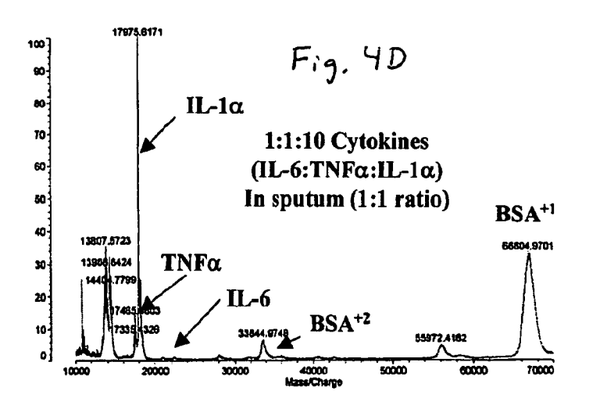

With this knowledge obtained from normalizing the spectrographs of the three individual cytokines, a complex mixture of the same three cytokines in equimolar ratios with a large excess of BSA in sputum was analyzed using mass spectrometry in a neat sample (i.e. no pre-purification step or wash). FIG. 4 shows the mass spectrographs of sputum (FIG. 4A), sputum plus BSA (FIG. 4B), equal amounts of three cytokines IL-6, TNF alpha and IL-1 alpha in a 1:1:1 ratio with a large excess of BSA of 1:1 sputum to cytokines (FIG. 4C), and of the three cytokines IL-6, TNF alpha and IL-1 alpha in a 1:1:10 ratio with a large excess of BSA of 1:1 sputum to cytokines (FIG. 4D). The ionization signal was set for the mass/charge of the TNF-alpha peak. All three cytokines and BSA could be distinguished in the mass spectrographs of the complex mixtures shown in FIGS. 4C and 4D. In FIG. 4C where the cytokine ratio of IL-6, TNF alpha and IL-1 alpha was 1:1:1, the TNF-alpha peak is the highest and IL-1 alpha is the smallest. While IL-1 alpha peak is small, it is consistent with what is expected from the single cytokine spectrographs for IL-1 alpha. In FIG. 4D where the cytokine ratio of IL-6, TNF alpha and IL-1 alpha was 1:1:10, the IL-1-alpha peak is now the highest and the IL-6 peak is now very small, but detectable.

Figure 5:
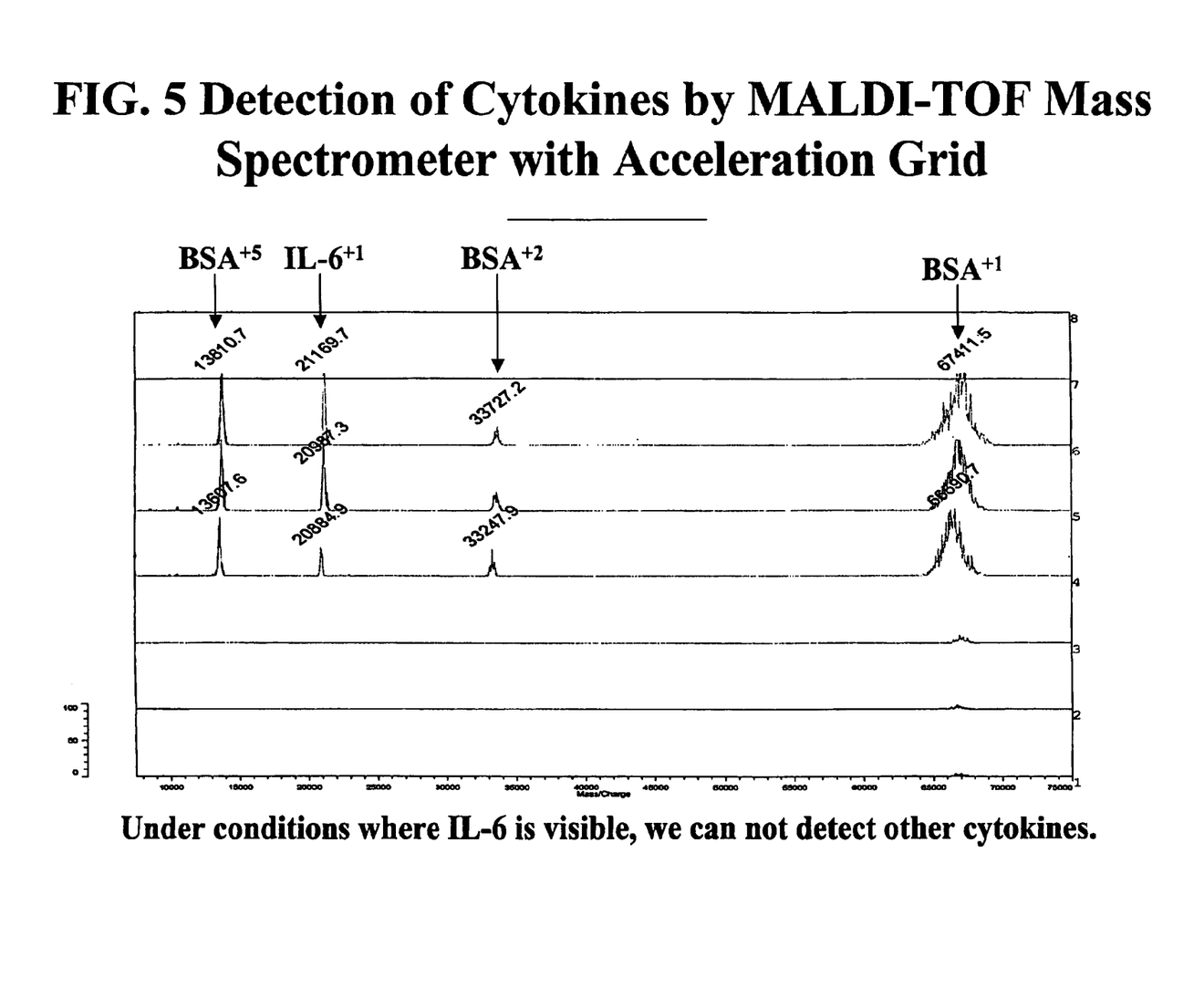
FIG. 5 is a graph illustrating Detection of Cytokines by MALDI-TOF Mass Spectrometer with Acceleration Grid that shows mass spectrograph patterns obtained for a complex mixture of IL-6, TNF alpha and IL-1-alpha and BSA at three different power levels; only the peak for IL-6 was seen.

A complex mixture of the same three cytokines in water with a large excess of BSA was also run on a Kratos MALDI linear mass spectrometer, this time with an acceleration grid system. As before, the ionization signal was set to that for TNF alpha. It was discovered that using a spectrometer using an acceleration grid does not provide high enough resolution to detect more than one cytokine in the complex mixture and sometimes cytokines are not detected at all. The results in FIG. 5 show that only IL-6 and BSA were detected when an acceleration grid was used. No peaks could be identified for TNF alpha and IL-1. When TNF alpha and IL-1-alphas were analyzed individually in different samples using the same conditions, there were no peaks corresponding to the mass/charge of known respective standards, although BSA was resolved. These two cytokines could not be resolved at any power level or condition using a mass spectrometer and the acceleration grid. Changes between three power levels shown in the figure and variation of the ionization signals (not shown) did not help to resolve peaks for the other known cytokines (IL-1 alpha and TNF alpha). Thus, mass spectrometers that employ an acceleration grid system will not detect cytokines reliably and will not detect more than one cytokine in a mixture. This may be because the acceleration grid deflects all but the most focused ions from the detector.

Thus, an embodiment of the present invention provides a method whereby multiple different cytokines in a complex mixture are clearly identified in a single mass spectrograph analysis of a neat biological sample (with no pre-preparation) using a gridless mass spectrometer operated in either a linear or reflectron mode. Either an ultraviolet laser or an infrared laser can be used. Using a high powered Einzel lens improves resolution. An Einzel lens is an electronic lens that focuses ions on to a narrow path down the flight tube of the mass spectrometer, creating less static and producing a more distinct peak in the final mass spectrograph. In some cases, PSD analysis is recommended, for example to distinguish between different molecules with the same or very close molecular mass. The samples can be analyzed with either pulsed or nonpulsed extraction. Mass spectrographs can be readily interpreted using well-developed rules for the interpretation of fragment ions.

Embodiments of the invention include using neat samples of sputum, bronchial lavage, exhaled breath condensate, and saliva or combinations thereof. Some biological samples, such as urine which contains many potassium or sodium phosphate ions, will need to be washed before mass spectral analysis. Thus urine will not be a neat sample. The present invention also pertains to methods of mass spectral analysis of more than one cytokine or immune modulator in a complex mixture that has been washed to remove unwanted ions before mass spectral analysis.

In sharp contrast to the methods of this invention, mass spectrometry was previously used to analyze standard proteomic preparations that typically involved harsh treatments that may have denatured the immune system modulators preventing their identification in a complex protein sample. Alternatively, liquid chromatography separations done to partially purify complex mixtures may remove some cytokines. Also some of the treatments used in preparing proteomic samples modify glycosylated molecules, including any immune system modulators, which may preclude their identification in a complex mixture, in part because the mass spectrometer may not be able to supply enough energy to ionize the glycosylated molecules. Importantly, it was discovered that resolution of more than one cytokine in a complex mixture of multiple cytokines or other immune system modulators like virokines, etc. could not be obtained if an acceleration grid was used in the mass spectrometer.

All mass spectrographs have a certain amount of noise in the signal along the base-line on the x-axis. Small peaks can be reliably distinguished from background noise if the height of the peak is at least 2.5 times greater than the local background noise. For comparison purposes, reliable mass spectrographs for known samples of pure compounds can be compiled using the MALDI mass spectrometer to obtain "gold standard" spectrographs for comparison with other mass spectrometry methods. MALDI mass spectrometers using either infrared lasers or ultra violet lasers can be used. Routine experimentation using known standards will determine the appropriate matrix for the immune system modulator being analyzed, and whether post source decay (PSD) analysis is advantageous to obtain sufficient resolution of the peaks for diagnostic purposes. We found that the sinapinic acid prepared in 70% acetonitrile (HPLC grade) and 30% acidified water (HPLC Grade) was the preferred matrix for analyzing all cytokines tested. In the related application, filed on Feb. 1, 2002 entitled Diagnosis of Pathogen Infections using Mass Spectral Analysis of Immune Modulators in Post-exposure Biological Samples, Jackman, this matrix was used in a MALDI-TOF mass spectrometer operated in linear mode without an acceleration grid used to analyze other cytokines including IL-1-beta, IL-2 and Interferon gamma. New infrared mass spectrometers have infrared lasers that can be tuned to different wavelengths to improve resolution. For some of the new instruments, a matrix of water may be suitable for resolution of multiple cytokines in a complex mixture.

Routine experimentation will also determine whether pulsed or nonpulsed extraction should be used. Pulsed extraction must be set to optimize for a particular size and mass range. Pulsed extraction can improve separation if the operator knows which cytokines are in the sample ahead of time. Pulsed extraction is therefore not recommended for screening samples for multiple immune system modulators because it will limit detection. However, if the operator is looking for a specific group of molecules that are close in size, pulsed extraction may be useful.

In the foregoing specification, the invention has been described with reference to specific embodiments thereof. It will, however, be evident that various modifications and changes may be made to the inventions without departing from the broader spirit and scope of the invention. Embodiments of the present inventions are described in further detail below, but are not limited by the examples.

EXAMPLES

Example I

Materials and Methods for Mass Spectrometry Cytokine Analysis

Purified cytokines were obtained from various manufacturers (Sigma, and RND Systems). All cytokines were recombinant human proteins.

Mass spectrometry was performed using a KRATOS AXIMA MALDI-TOF mass spectrometer. Analysis was performed using the linear detector with and without pulsed extraction. The MALDI-TOF was calibrated with cytochrome C or BSA (bovine serum albumin) in Sinapinic acid matrix. Purified cytokine standards were stored at $-70°$ C. before being reconstituted to equal molar concentrations based on manufacturer's determination of the amount of cytokine. BSA was added by the manufacturer to all cytokine samples. Human sputum was obtained from a healthy donor. Sputum was obtained according to established methods by forceful exapectoration. Cytokines were mixed with sputum samples at the reported ratios based on volume.

Samples were prepared for MALDI analysis as follows. Sinapinic acid or alpha cyano matrix was used for all analysis. Experiments with other matrices indicated that sinapinnic acid was the preferred matrix for cytokine analysis. All pictured analyses were performed with sinapinic acid prepared in 70% acetonitrile (HPLC grade) and 30% acidified water (HPLC Grade). Water is acidified with addition of 0.1% trifluoroacetic acid. 0.3 microliter of matrix is used to coat the substratum that in this case is the slide itself A filter can also be used as a matrix. Before fully dried, 0.3 microliter of sample test material is added to the matrix and 0.3 microliter of additional matrix is added to the sample test material. The matrix-saturated sample is allowed to dry prior to placing in MALDI-TOF. Spectrographs were obtained from pure samples and mixtures using the same sample preparation conditions. To obtain standard spectrographs of pure samples of the immune system modulators being analyzed for comparison purposes, each pure sample was run individually.

The mass spectrometer should be periodically recalibrated so that the standard spectrographs obtained for pure samples of immune system modulators can be used for comparison purposes without redoing the standards. The daily frequency of calibration depends on the number of samples being run and variability among mass spectrometers.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method for analyzing the presence of one or more immune system modulators in a complex mixture using mass spectrometry, comprising the steps of:
   a. obtaining a complex mixture for mass spectral analysis, wherein the complex mixture includes exhaled breath condensate,
   b. placing a sample of the complex mixture including the exhaled breath condensate on a substratum suitable for use in a mass spectrometer,
   c. saturating the sample with matrix material,
   d. allowing the sample to dry,
   e. inserting the sample into a mass spectrometer, and
   f. processing the sample in the mass spectrometer to obtain a mass spectrograph of the complex mixture including the exhaled breath condensate, wherein said processing includes determining, from the mass spectrograph, whether the sample of exhaled breath condensate includes one or more immune system modulators comprising at least a fragment of a protein.

2. The method of claim 1, further including the steps of:
   g. obtaining a known sample of pure immune system modulator standard comprising a protein for a particular immune system modulator comprising the protein,
   h. placing the known sample on a substratum suitable for use in a mass spectrometer,
   i. repeating steps c–f for the known sample to obtain a mass spectrograph of the pure immune system modulator standard comprising the protein,
   j. comparing the mass spectrograph of the complex mixture to the mass spectrograph of the pure immune system modulator standard comprising the protein, and
   k. determining whether the complex mixture includes the particular immune system modulator based on whether one or more peaks of the mass spectrograph of the pure immune system modulator standard comprising the protein are identified in the mass spectrograph of the complex mixture.

3. The method of claim 2, wherein the complex mixture requires no pre-purification step.

4. The method of claim 2, wherein the complex mixture including the exhaled breath condensate has been washed to remove unwanted ions.

5. The method of claim 2, wherein the immune system modulator has a molecular mass of 30 kilo Daltons or less.

6. The method of claim 2, wherein the immune system modulator is a cytokine.

7. The method of claim 2, wherein the immune system modulator is a membrane receptor or fragment thereof.

8. The method of claim 1, wherein the mass spectrometer is a matrix assisted laser desorption/ionization (MALDI) mass spectrometer.

9. The method of claim 1, wherein the mass spectrometer is operated in a linear mode.

10. The method of claim 1, wherein the mass spectrometer is operated in a reflectron mode.

11. The method of claim 1, wherein the mass spectrograph is obtained using pulsed extraction.

12. The method of claim 1, wherein the matrix is a sinapinic acid matrix.

13. The method of claim 1, wherein step (f) further comprises the step of employing post-source decay (PSD) analysis.

14. The method of claim 1, wherein the immune system modulator is selected from the group comprising cytokines, chemokines, and virokines.

15. The method of claim 1, wherein the mass spectrometer uses either infrared lasers or ultra violet laser.

16. The method as in claim 1, wherein the sample is washed before it is placed on the substratum.

17. The method of claim 1, wherein each of the one or more immune system modulators in the exhaled breath condensate is released by mammalian cells.

18. The method of claim 1, wherein each of the one or more immune system modulators in the exhaled breath condensate is excreted by one or more pathogens.

19. The method as in claim 1, wherein the mass spectrometer of steps (e) and (f) is a gridless mass spectrometer.

20. The method of claim 1, wherein the one or more immune system modulators includes multiple immune system modulators, and wherein step f. comprises:
- obtaining multiple spectrographs each corresponding to a different one of the multiple system modulators;
- normalizing each of the multiple spectrographs to a common maximum ionization signal among the multiple spectrographs; and
- overlaying and aligning the normalized multiple spectrographs.

21. A method for analyzing the presence of one or more molecular markers of infection in a complex mixture using mass spectrometry, comprising the steps of:
- a. obtaining a complex mixture for mass spectral analysis, wherein the complex mixture includes exhaled breath condensate,
- b. placing a sample of the complex mixture including the exhaled breath condensate on a substratum suitable for use in a mass spectrometer,
- c. saturating the sample with matrix material,
- d. allowing the sample to dry,
- e. inserting the sample into a mass spectrometer, and
- f. processing the sample in the mass spectrometer to obtain a mass spectrograph of the complex mixture including the exhaled breath condensate, wherein the method further includes
- obtaining a known sample of pure molecular marker of infection standard for a particular molecular marker of infection comprising at least a fragment of a protein,
- placing the known sample on a substratum suitable for use in a mass spectrometer,
- repeating steps c–f for the known sample to obtain a mass spectrograph of the pure molecular marker of infection standard,
- comparing the mass spectrograph of the complex mixture to the mass spectrograph of the pure molecular marker of infection standard, and
- determining whether the complex mixture includes the particular molecular marker of infection, comprising at least a fragment of a protein, based on whether one or more peaks of the mass spectrograph of the pure molecular marker of infection standard are identified in the mass spectrograph of the complex mixture.

22. The method as in claim 21, wherein the molecular marker of infection is a prion, a pathogen-encoded DNA fragment, a pathogen-encoded protein or a peptide.

23. The method as in claim 21, wherein the mass spectrometer of steps (e) and (f) is a gridless mass spectrometer.

24. A method for analyzing the presence of one or more immune system modulators in a complex mixture using mass spectrometry, comprising the steps of:
- a. obtaining a complex mixture for mass spectral analysis, wherein the complex mixture includes exhaled breath condensate having the one or more immune system modulators therein,
- b. placing a sample of the complex mixture including the exhaled breath condensate on a substratum suitable for use in a mass spectrometer,
- c. saturating the sample with matrix material,
- d. allowing the sample to dry,
- e. inserting the sample into a mass spectrometer, and
- f. processing the sample in the mass spectrometer to obtain a mass spectrograph of the complex mixture including the exhaled breath condensate, wherein the one or more immune system modulators includes multiple immune system modulators, and wherein step f. comprises:

obtaining multiple spectrographs each corresponding to a different one of the multiple system modulators;

normalizing each of the multiple spectrographs to a common maximum ionization signal among the multiple spectrographs; and overlaying and aligning the normalized multiple spectrographs.

* * * * *